(12) United States Patent  (10) Patent No.: US 7,674,261 B2
Garito et al.  (45) Date of Patent: Mar. 9, 2010

(54) ELECTROSURGICAL INSTRUMENT WITH ENHANCED CAPABILITY

(75) Inventors: Jon C. Garito, Oceanside, NY (US); Alan G. Ellman, Oceanside, NY (US)

(73) Assignee: ElliQuence, LLC, Oceanside, NY (US)

( * ) Notice: Subject to any disclaimer, the term of this patent is extended or adjusted under 35 U.S.C. 154(b) by 729 days.

(21) Appl. No.: 11/090,858

(22) Filed: Mar. 28, 2005

(65) Prior Publication Data

US 2006/0217700 A1  Sep. 28, 2006

(51) Int. Cl.
*A61B 18/18* (2006.01)
(52) U.S. Cl. .............................. 606/42; 606/34; 606/37; 606/39; 606/40
(58) Field of Classification Search .............. 606/32–52
See application file for complete search history.

(56) References Cited

U.S. PATENT DOCUMENTS

| | | | | |
|---|---|---|---|---|
| 3,699,967 | A * | 10/1972 | Anderson | 606/37 |
| 3,730,188 | A * | 5/1973 | Ellman | 606/37 |
| 4,463,759 | A * | 8/1984 | Garito et al. | 606/42 |
| 5,626,575 | A * | 5/1997 | Crenner | 606/34 |
| 6,652,514 | B2 * | 11/2003 | Ellman et al. | 606/37 |
| 6,740,079 | B1 * | 5/2004 | Eggers et al. | 606/34 |
| 7,217,269 | B2 * | 5/2007 | El-Galley et al. | 606/34 |
| 7,353,068 | B2 * | 4/2008 | Tanaka et al. | 700/17 |
| 2001/0029315 | A1 * | 10/2001 | Sakurai et al. | 600/101 |
| 2003/0163124 | A1 * | 8/2003 | Goble | 606/37 |
| 2004/0030328 | A1 * | 2/2004 | Eggers et al. | 606/34 |
| 2004/0054365 | A1 * | 3/2004 | Goble | 606/34 |

* cited by examiner

*Primary Examiner*—Roy D Gibson
*Assistant Examiner*—Kaitlyn E Helling (57) ABSTRACT

An electrosurgical instrument for use by a surgeon that provides additional features and benefits compared with known designs. The operating mode as well as other operating parameters, especially power level, can be preset by the surgeon before commencing the procedure. Five operating modes are available using a three-button fingerswitch handpiece and a 3-way footswitch, including three unipolar modes and two bipolar modes over a full range of power levels including a new turbo mode for treating heavy bleeders.

9 Claims, 7 Drawing Sheets

Fig. 11

ELECTROSURGICAL INSTRUMENT WITH ENHANCED CAPABILITY

RELATED APPLICATION

Commonly-owned US application, application Ser. No. 10/761,774, filed Jan. 22, 2004, entitled "Dual-Mode Electrosurgical Instrument".

The invention is directed to an electrosurgical instrument, and in particular to an electrosurgical instrument with an intelligent selection system and improved output modes.

BACKGROUND OF INVENTION

Electrosurgical instruments are well known and widely used in the medical, dental, and veterinarian fields. They offer the capability of precision cutting and coagulation with electrosurgical currents preferably in the megacycle range using an RF probe or handpiece with, for example, needle, ball, or loop electrodes in a unipolar operating mode or with a forceps or other electrode in a bipolar operating mode. Ellman International, Inc. makes available an electrosurgical instrument for Radiosurgery which provides on its front panel connectors for receiving the plug of a cable-connected unipolar handpiece and a ground or indifferent plate, as well as connectors for receiving the plug of a cable-connected bipolar electrode. Several forms of such an instrument are described in U.S. Pat. Nos. 5,954,686, and 6,652,514, both of whose contents are incorporated herein by reference. The instruments described in those patents are characterized by different modes and sub-modes of operation. For example, the instruments have five possible operating modes, a cutting mode, separable into CUT and CUT/COAG sub-modes, and a coagulation mode, separable into HEMO, FULGURATE, and BIPOLAR sub-modes.

In a typical surgical setting using such an instrument, a surgeon may first use a handpiece while the instrument is in its cutting mode to perform a desired cutting procedure and then desire to use the same handpiece for coagulation of blood vessels while the instrument is in its coagulation mode. To this end, the electrosurgical instrument has on its front panel push buttons or switches for activating internal circuitry for switching the electrosurgical instrument from its cutting to its coagulation mode or vice-versa. A current electrosurgical instrument contains a power-supply-controlled radio-frequency (RF) oscillator which generates RF currents typically in the megacycle range as high-frequency AC waves. For most cutting purposes, the AC waveform is fully filtered to produce an approximate DC waveform. For most coagulation purposes, the AC waveform is partially rectified (commonly half-wave rectification) to produce the characteristic half-wave rectified waveform. This is accomplished by switching in certain rectifier and filter components for the cutting mode, and switching in certain rectifier components for the coagulation mode. This is well known in the art and further description is unnecessary. Suffice to say, the switching action occurs inside the instrument when the front panel controls are activated by the surgeon.

To simplify mode selection by the surgeon, it is known to place on the handpiece two finger-activated switches that can be connected by appropriate wiring to the electrosurgical instrument and wired in parallel with the front panel switches so that activation of either the finger switches on the handpiece or the front panel switches will allow mode selection. This is similar to the connection and operation of a footswitch that can be used by the surgeon to activate and deactivate the RF currents.

A complication in the use of such instruments is the variety of surgical procedures to which the instrument can be applied. Each surgical procedure typically requires not only a particular electrosurgical mode, such as cut or cut/coag, or hemo, but also may require a different set of mode conditions, such as the power setting and perhaps a different time duration of power application.

The related application, application. Ser. No. 10/761,774, the contents of which are herein incorporated by reference, describes an electrosurgical instrument that allows successive use of unipolar and bipolar handpieces, but the operating conditions must be chosen for each use by the use of switches on the front panel of the instrument. No µ-controller/computer is present.

SUMMARY OF INVENTION

A principal object of the invention is an electrosurgical instrument for use by the surgeon in a manner that depends primarily but not necessarily always on the surgical procedure to be employed.

Another object of the invention is an electrosurgical instrument with enhanced capability, including but not limited to more useful operating modes than was heretofore available, a larger range of power outputs, built-in operating modes controllable by console switches as well as fingerswitch and footswitch controls.

These objects are achieved in accordance with one aspect of the invention by an electrosurgical system with enhanced capability in comparison with known instruments. It includes one or more of the following features:

a compact source of high power RF energy to be employed for a variety of radiosurgery procedures;

special accessories including preset retrievable mode and power output level settings;

improved control software to boost the operational applications to five operating modes that include CUT, CUT/COAG, HEMO, BIPOLAR HEMO, and BIPOLAR TURBO; the latter two bipolar modes providing high and low output powers to provide the vitality for special applications;

a triple footswitch control for controlling unipolar and dual bipolar applications, and a three-button fingerswitch handpiece for separately controlling three monopolar modes, respectively—these two control accessories can thus control and activate any desired selected modes with the instrument's preset output power capabilities (unipolar and monopolar are used interchangeably herein);

all output parameters can be adjusted prior to the surgical procedure, thus eliminating the need to go back to the electrosurgical instrument to make adjustments during the procedure.

The electrosurgical instrument of the invention can be designed to operate with manually-chosen operating conditions, and also incorporates one or more sets of stored or preset operating modes and conditions that allows the surgeon to select a particular set customized for the particular procedure to be carried out. So if procedure A is to be carried out, then set A is automatically selected, set A prescribing the electrosurgical mode of operation and one or more of the mode conditions specific to the selected procedure. Similarly, if procedure B is to be carried out, then set B is automatically selected, set B prescribing the electrosurgical mode of operation and one or more of the mode conditions specific to the selected procedure, and so on.

The selection system is incorporated in a preferred embodiment in a built-in non-volatile memory that stores the setting last used by the surgeon for a particular procedure. The setting is automatically selected when the surgeon operates a fingerswitch on the handpiece or one of the footswitch controls. The settings can be overridden at any time by manually changing the power level, for example, at the instrument.

The enhanced instrument can incorporate handpieces with built-in electrodes and a mode-selecting capability as described in the '514 patent, or can be used if desired with the standard handpiece.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF PREFERRED EMBODIMENTS

Figure 1:
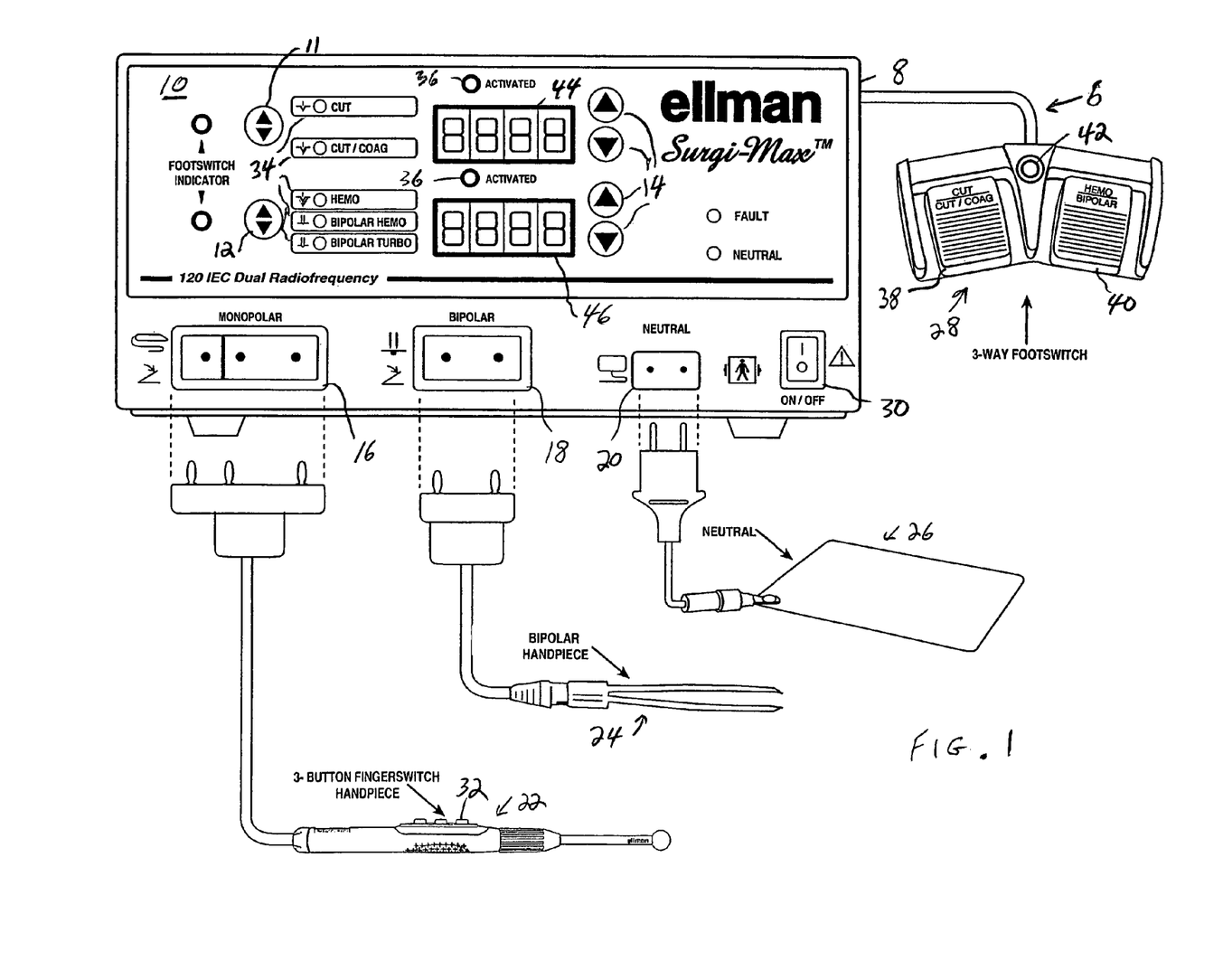
FIG. 1 is a schematic view from the front of one form of electrosurgical instrument in accordance with the invention.

One form of an electrosurgical instrument 6 according to the invention is illustrated in FIG. 1. It comprises a system unit 8 having a box-like housing comprising at the front a control panel 10 for the instrument. The control panel includes touch switches 11, 12 for toggling among the five cutting or coagulation or hemo modes and touch switches 14 for controlling the power output by increasing or decreasing in steps the power, the percentage of full power of which is indicated by upper and lower digital displays showing all 8's in the drawing. At the bottom are output female connectors 16, 18, 20 for plugging in, respectively, at the left, a fingerswitch-controlled unipolar handpiece 22; at the center, a bipolar handpiece or forceps 24; and at the right a single or split neutral plate 26. An on-off power switch 30 is at the far right. The circuitry used to provide a fingerswitch-controlled unipolar handpiece may be of the type described in connection with the control unit 50 of U.S. Pat. No. 4,463,759, whose contents are herein incorporated by reference, which circuitry is in this case incorporated in the console unit 8. A connector (not shown) is provided at the side for receiving a triple or 3-way footswitch 28. Both the unipolar and bipolar handpieces can be simultaneously connected to the system unit 8 and operated in any order without touching the system unit or the control panel when the control panel has been manually set or activated at the desired powers on the basis of the previous use. For example, if the surgeon determines that s/he is going to perform a cutting procedure with a particular electrode, then s/he can set the cutting mode power on the upper digital display to, say, 50% (=60 watts in the preferred embodiment) by the upper up/down button 14. (Preferably, these units are designed to supply as high as 120 watts of RF power to either handpiece.) For coagulation with the bipolar handpiece, s/he may desire to use, say, 30% or 36 watts, which can also be set on the lower digital display by the lower up/down power button 14. In this first embodiment, the internal circuitry is controlled in a known manner so that, when the fingerswitch unipolar handpiece 22 is activated or the left footswitch section 38, then RF power can be supplied to the electrode in the unipolar handpiece 22. However, when it is desired to use the bipolar handpiece 24, then the right section 40 of the footswitch 28 is depressed, which then supplies RF power to the forceps of the bipolar handpiece or any other bipolar handpiece plugged into the bipolar connector 18. For bipolar turbo-hemo action, a center footswitch button 42 is supplied. The latter always activates the bipolar handpiece 24. Software control ensures that, while the machine mode is selected such that the fingerswitches on the unipolar handpiece can be used to apply power to the electrode (footswitch mode non-selected), only the latter or the left footswitch can be used to apply power to the unipolar handpiece. This prevents power selected for the unipolar handpiece to be applied to the bipolar handpiece, and vice-versa. On the other hand, when it is not intended to use the unipolar handpiece and the footswitch mode is selected, then the footswitch can be used to operate the biipolar handpiece by depressing the right footswitch or the center button switch 42.

Figure 2:
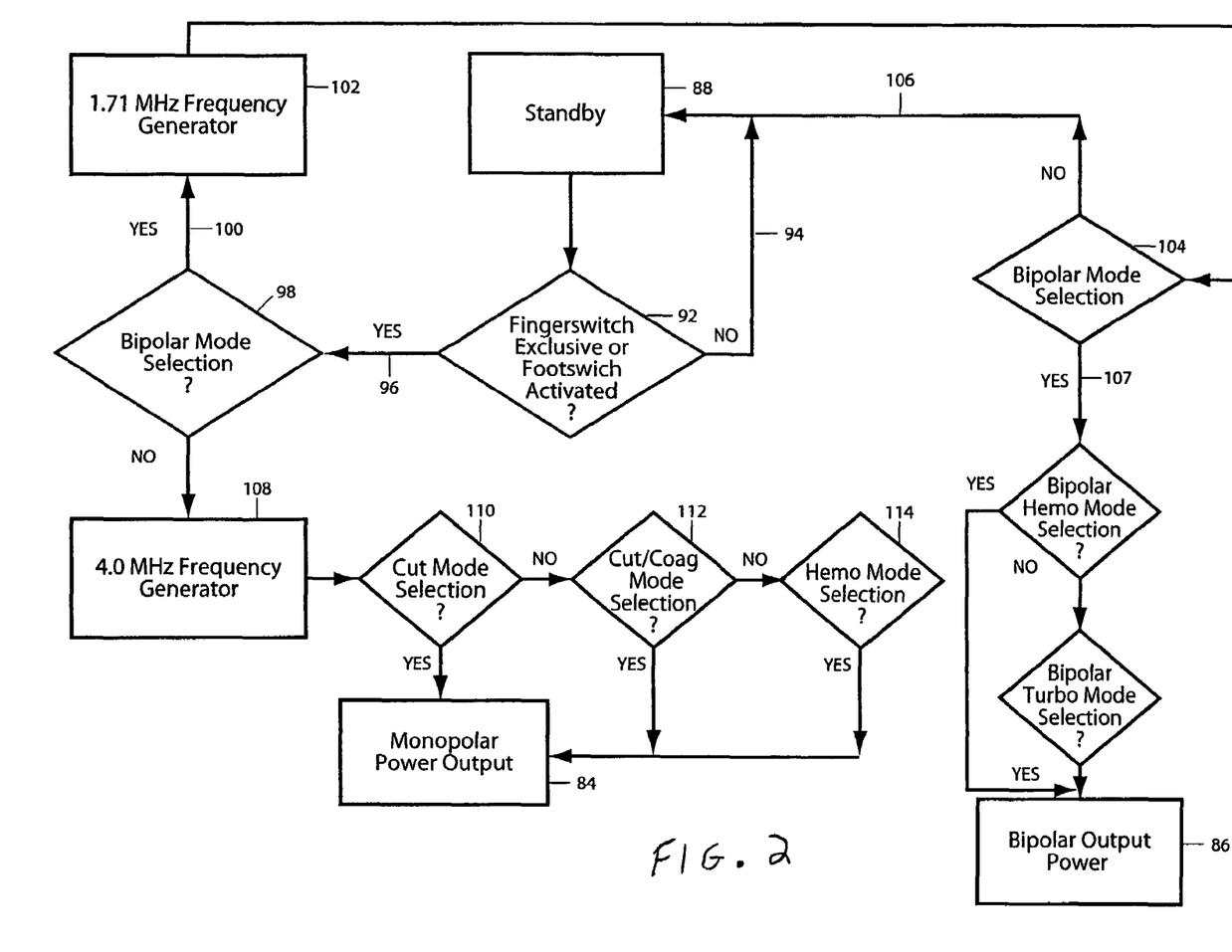
FIG. 2 is a combined flow chart and circuit block diagram of one form of system circuitry for the electrosurgical instrument of FIG. 1.

One form of the RF circuitry and its operation to achieve the foregoing is illustrated in the combined flow chart and block diagram of FIG. 2. The blocks 102, 108 at the left contain two independent conventional RF oscillators generating, preferably, RF oscillations at a first 4.0 and second 1.71 MHz frequency, respectively. As will be explained in greater detail below (see FIG. 6), a conventional programmed μ-controller generates a selection signal under software control to select for operation either the 4.0 MHz oscillator or the 1.71 MHz oscillator. Both oscillators are constantly on when the power switch is activated, and the μ-controller selection determines which of the first or second frequencies are outputted, resulting in an RF carrier at either the first (4.0 MHz) frequency to the unipolar output or the second (1.71 MHz) frequency to the bipolar output. The processing of the RF carrier is then processed similarly to that in the '686 patent, by passing through a pre-amplifier and then inputted to a conventional modulator stage. Also input to the modulator stage is a modulating signal. The modulations referred to are the different output waveforms used for the known CUT, CUT/COAG, HEMO, BIPOLAR HEMO modes and a new BIPOLAR TURBO mode. These typically are: CUT-CW (full-wave rectified and filtered) output with maximum average power; CUT/COAG-full-wave rectified but unfiltered, deeply modulated, at 37.5 or 75 Hz rate, envelope with approximately 70% average to peak power ratio; HEMO-and bipolar HEMO half-wave rectified and unfiltered, deeply modulated, at 37.5 or 75 Hz rate, envelope with approximately 35% average to peak power ratio. As will be explained below, a new form of modulation with a smaller duty cycle but at higher power, called Turbo Mode bipolar is now included. This is, for example, a burst of amplitude modulated RF energy which occurs every 26 milliseconds for 13 milliseconds. The sequence is: the RF burst power increases gradually for the first 5 milliseconds, stays at maximum for 3 milliseconds, and then gradually decreases in power for the final 5 milliseconds. The applications for this new electrosurgical RF mode will be explained below. The invention is not limited to these quantities.

The RF power generating circuitry may be of the well known tube-type described in U.S. Pat. No. 3,730,188, whose contents are herein incorporated by reference, which is capable of generating a fully-rectified, filtered RF current for cutting, a full-wave rectified current for combining cutting and coagulation, and a half-wave rectified current for coagulation. Alternatively, the RF power generating circuitry can be of the well-known solid-state type capable of generating the same kinds of waveforms. Those skilled in the art will know how to produce the turbo mode modulation from the description given. The RF circuitry, as such, is not part of the present invention, as such circuits are well-known in the prior art. In this case, the RF circuitry provides two different frequencies of operation, a first high frequency in the range of 3.8-4.0 MHz, 4.0 being preferred, and a second high frequency in the range of 1.7-2.0 MHz, which is easily obtained by providing a known RF generator that provides outputs at double these first and second higher frequencies and providing a simple known divide-by-two circuit for obtaining dual outputs at the first or second frequencies, respectively. Both outputs can be separately amplified and processed and made available at the console's output connectors depending on the switches activated. Aspects of the present invention are not limited to the dual-frequency output operation.

After the modulated carrier has been generated, it is processed through a standard driver, a transformer, and a power amplifier controlled by a bias signal and whose input is monitored for safety's sake by a power tester circuit under control of the μ-controller.

In this embodiment, the instrument is software controlled with the user supplying the switch inputs. One form of software control is illustrated by the flow chart depicted in FIG. 2. When the on-off switch 30 is toggled on, the microcontroller (not shown) is placed in its standby condition represented by block 88 for manual operations. For manual operation, the first action by the user is to select one of the up/down toggle switches 11, 12 on the front panel. If the top switch 11 is activated, then the operation will be exclusively by the fingerswitch handpiece 22. This action activates a light on one of the top two indicators 34 to indicate which of the CUT and CUT/COAG modes is selected. Each switch depression toggles the operation between the two modes. Additionally, an activation light 36 above the upper display 44 is turned on and the display lights up to indicate the power level setting. If the various hemo modes are to be used, then the lower up/down button 12 is activated which similarly toggles among the lower hemo selections 34, activating a light on the selected mode indicator 34 and activated light 36 above the lower display 46. These actions are represented by the diamond test block 92. The fingerswitch handpiece 22 operates exclusively of and independent from the footswitch mode selection for all unipolar modes. This ensures that RF currents are available exclusively and at all times at one of the sockets 16, 18. If no such user action has occurred, tested at block 92, the CPU returns 94 to its standby condition. If a selection has been made 96, control is passed to the test block 98, which tests whether lower switch 12 has selected the hemo unipolar or bipolar modes. If yes 100, the circuitry to generate the 1.7 MHz carrier is selected at block 102, and control passes to the test block 104 which tests whether the right footswitch 40 has been pressed, which is the only way by which 1.7 MHz currents can be made available at the bipolar handpiece socket 18. If no, the CPU returns 106 to its standby mode; if yes 107, RF energy is supplied to the bipolar handpiece socket 22 represented by block 86. A similar sequence determines whether bipolar hemo or bipolar turbo has been selected. Each of these selections it will be understood controls a software routine that determines which form of modulation is added to the 1.7 MHz carrier to supply at the output the desired electrosurgical energy.

Returning now to test block 98, if the answer is that bipolar was not selected, then the circuitry to generate the 4.0 MHz carrier is selected at block 108, and control passes to the test block 110 which tests whether the cut mode selection has been made. If yes, the circuitry that generates the 4.0 MHz carrier is directed to the monopolar power output socket 16 represented by the block 84. If no, control passes to test block 112 that tests whether the cut/coag selection was made. If yes, the 4.0 MHz carrier is directed to the monopolar power output socket represented by the block 84. If no, control passes to test block 114. If the hemo mode selection was made, the 4.0 MHz carrier is also directed to the monopolar power output socket represented by the block 84. If no selection of hemo mode was made, then the default exit (not shown) is to the standby mode and a message will be displayed indicating to the user that no selections were made.

In a first major mode of operation:

a. the right footswitch 40 can control operation of the second lower frequency generator 102 which can be supplied only to the bipolar handpiece 24, the left footswitch 38 or the handpiece fingerswitch controls operation of the first higher frequency generator 108 which can be supplied only to the unipolar handpiece 22, and in this way the surgeon can know that the choice he makes of one or the other controls determines whether he intends to use lower or higher MHz frequencies in the procedure, also indicated on the display panel by the correspondingly lit lights.

In a second major mode:

b. the footswitch can be used to control both monopolar and bipolar operations at either of the handpieces, if no fingerswitches on the handpiece are pressed. The software precludes simultaneous operation of both the footswitch and a fingerswitch.

A third major mode:

allows all operations to be controlled manually from the front instrument panel 14.

In these operations, the ground plate 26 is always attached to the patient, and the surgeon can perform any desired unipolar or bipolar electrosurgical procedure. When both the unipolar and bipolar handpieces are plugged into the instrument console 8, then the desired operating conditions for each can be preset as desired. Then whichever handpiece is picked up and operated by the surgeon will automatically determine which is supplied with the appropriate RF currents at the preset power level. Thus, if the bipolar handpiece is selected and the footswitch activated, the bipolar handpiece will be supplied with 1.7 MHz currents at the power setting last selected by the user. On the other hand, if the unipolar handpiece is selected and its fingerswitch 36 activated, the unipolar handpiece will be supplied with 4.0 MHz currents at the power setting last selected by the user. This operates on a first-come, first-served basis, which thus allows the surgeon to use the CUT mode for cutting with the unipolar handpiece followed with the bipolar handpiece for closing off any bleeders exposed during the cutting.

What has so far been described are several ways of operating the instrument with conventional or standard handpieces. In accordance with a further feature of the present invention, instead of or in addition to using the manual mode of operation, an automatic mode is incorporated that is determined by the procedure to be performed by the surgeon or by the handpiece selected by the surgeon for the procedure. Preferably, the desired mode is selected by plugging an intelligent handpiece into the instrument. Examples of such handpieces are described in connection with FIGS. 4-13 of the previously referred to '514 patent. Briefly, each "smart" or dedicated handpiece has a built-in impedance, for example, a resistor whose value when sensed can then be used to select an operating mode of the system unit as described in detail in the '514 patent. The same use of different resistors in the standard 3-button handpiece is also preferably employed to select one of the unipolar operating modes by pressing one of the three buttons associated with that operating mode. We prefer in the enhanced system of the present invention to employ an internal non-volatile memory, such as, for example, an EEPROM, incorporated in the handpiece or preferably in the system unit 8. The EEPROM has the benefit that, if changes in the procedure conditions become necessary, the EEPROM can be reprogrammed externally, as is well known in the art.

Figure 6:
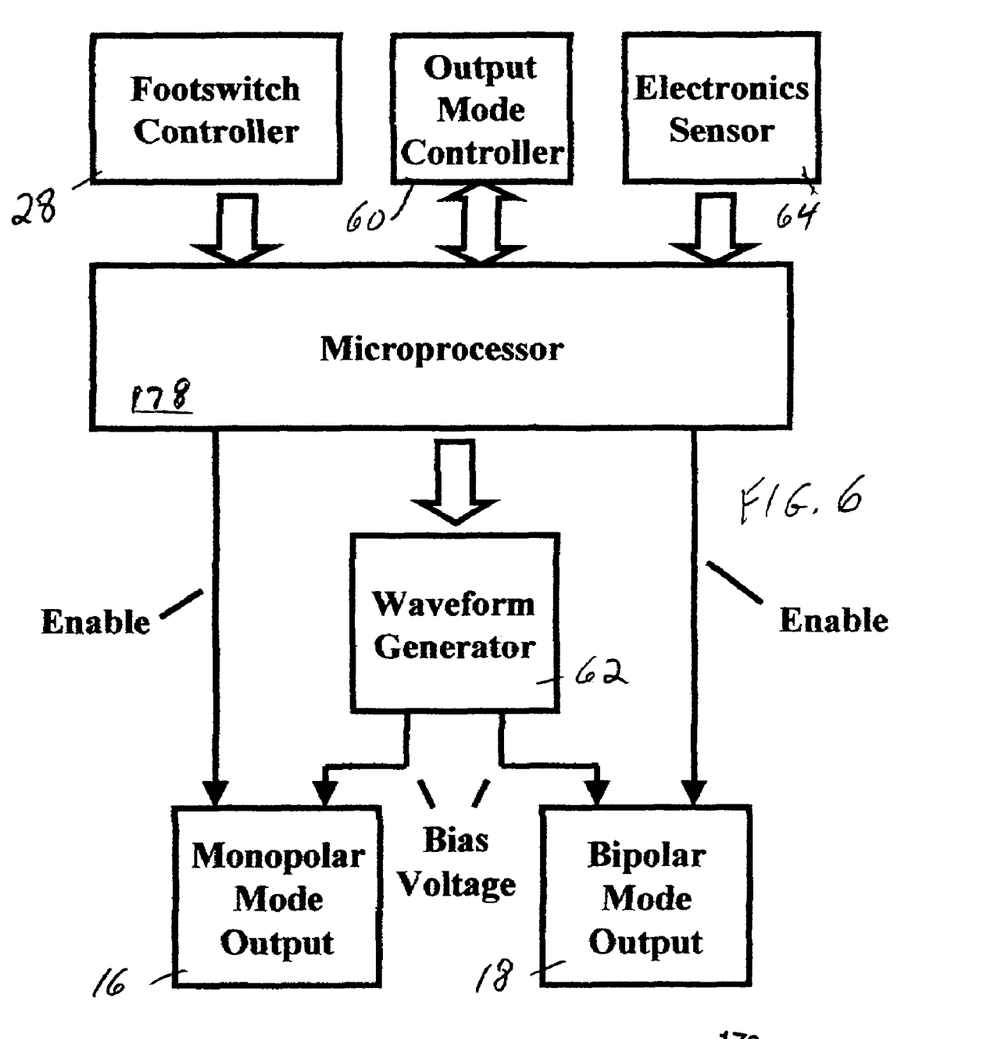
FIG. 6 is a block diagram of another section of circuitry including the μ-controller for the electrosurgical instrument of FIG. 1.
Figure 10:
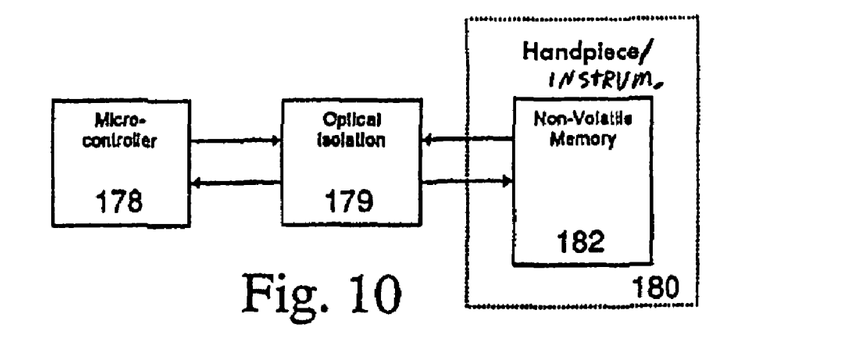
FIG. 10 is a block diagram showing how the handpiece of FIG. 9 or instrument can be interfaced to a u-controller in the electrosurgical instrument.

In the previously described operation, the preset operation is readily achieved by the use of the non-volatile memory inside the instrument. The EEPROM and μ-controller cooperate in a straightforward manner so that the EEPROM stores in a memory location a word representing, for example, the last power setting for each of the five modes of operation. When the instrument is first turned on, those stored words can be retrieved whenever the appropriate mode is selected. So, for example, if the last time the CUT mode was used with the fingerswitch handpiece 22, then the power level manually selected by the surgeon is stored in the EEPROM. When the fingerswitch handpiece 22 is again used in the CUT mode, the computer word representing the last power setting is retrieved and used to adjust in a known way the electrical bias on the power output amplifier for the first frequency so that that power level is selected and the value displayed on the upper display 44. This is depicted in FIG. 6, described below. If the surgeon should change the power level, then the new power level is stored in the EEPROM, and then if s/he switches to a different mode or shuts down the instrument, then the changed power is retained such that, when that mode is again used the last used-power level is automatically set in the instrument. The connections between the μ-controller represented at 178 in FIG. 10 and the EEPROM 182 are schematically indicated in FIG. 10. In this particular illustration, the EEPROM is shown in the handpiece 180, but the preferred embodiment places the EEPROM in the instrument console 8. The two blocks may be interconnected by optical isolation represented by the block 179.

Figure 11:
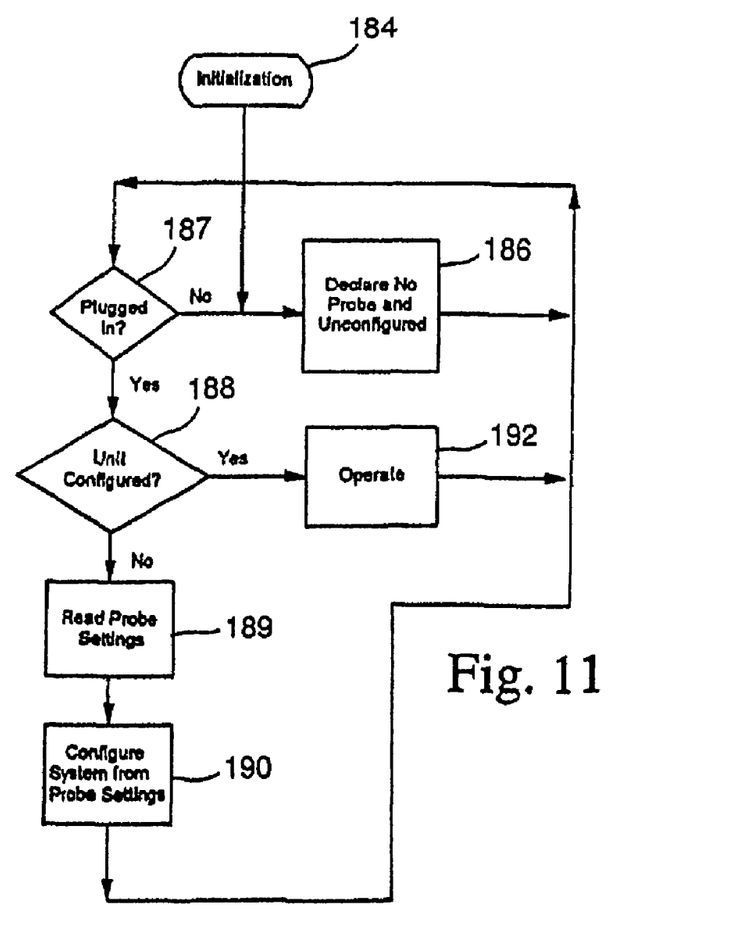
FIG. 11 is a flow chart indicating how the electrosurgical instrument can be programmed to operate with a particular setting according to the invention.

FIG. 11 is a flow chart that schematically illustrates how the selected mode and power, can be actually implemented in the instrument. The starting point is the initialization block 184. If no handpiece, sometimes referred to for brevity herein as "probe", has been connected to the instrument or it is unconfigured 186, the program branches to block 187 to check whether a probe has been connected. If the answer is no, the program loops back to block 187. If the answer is yes, the program falls through to block 188 to check whether the system is configured. If the answer is no, then, under control of the program, the system controller 178 accesses the internal EEPROM 182, reads 189 the EEPROM settings, and at block 190 then configures the instrument (system) to the correct mode and condition settings. The program then returns to block 187, proceeds then to block 188 and branches to the right to the block 192 which allows operation including if desired display of the operating parameters to the user based on the EEPROM settings.

In the read probe block 189, the μC receives an unambiguous indication of what buttons are physically on the probe and what modes they initiate. A probe could be configured to allow a unit to work only in one or certain modes, and could also be configured to allow the electrosurgical unit to put out only certain ranges of power in each allowed mode. In addition, if desired, the probe memory 182 could be used to implement the number of uses or elapsed time of use functions. A new probe might be set to 50 uses or 100 minutes of use to retain its reliability. The mode and condition-setting functions can be incorporated in the probe or handpiece as just described or in the electrosurgical instrument or in both. In the case of the electrosurgical instrument, there are a number of different ways in which a handpiece or footswitch press can select the mode and conditions of a particular procedure. The simplest way as described in the '514 patent is to incorporate in the instrument a conventional look-up table that contains the mode and operating conditions for a number of different procedures, with the look-up table responding to a particular control signal (key) from the handpiece to vector to a subroutine which, equivalent to the surgeon's activation of the front panel switches, automatically switches the electrosurgical instrument to the correct mode and sub-mode and automatically sets the power to a specific value.

Or, as another example, described in the '813 patent, a handpiece can be provided that is tailored for surgical procedures carried out with the instrument set at the cutting mode and the Cut or Cut/Coag sub-mode. The handpiece has incorporated in it a known blade electrode. The handpiece tailored for cutting has a resistor of say 40 ohms connected to one of the finger switches, so when that finger switch is pressed, a control signal is sent to the instrument housing the microcontroller, and the μ-controller then activates the routine that sets the desired power level for the desired procedure.

Figure 3:
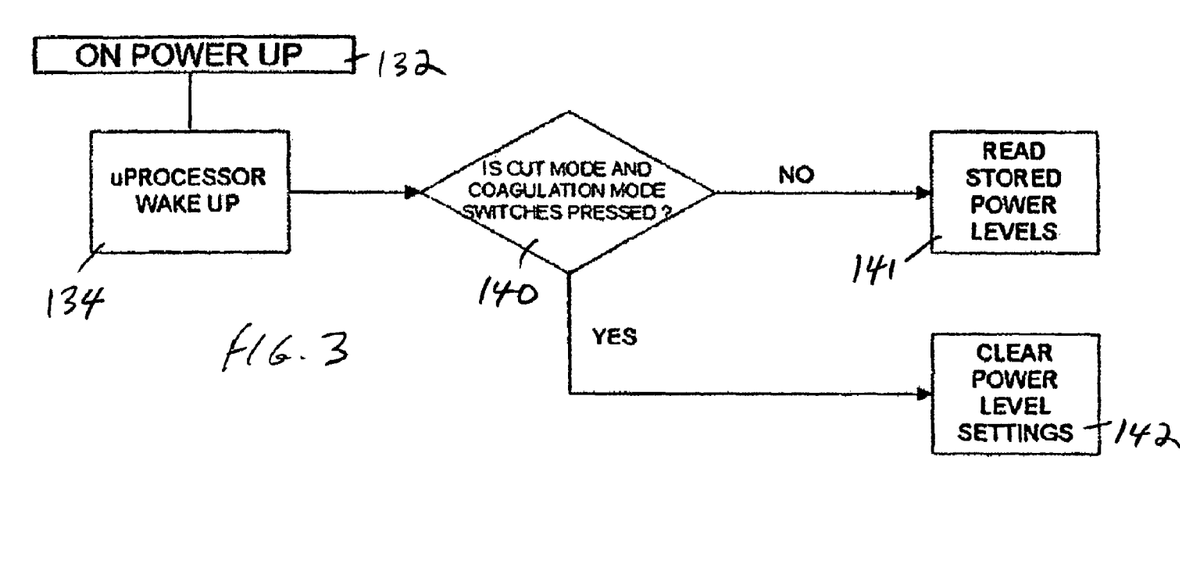
FIGS. 3 and 4 are flow charts illustrating the primary software controlled operations upon powering up the electrosurgical system in accordance with the invention.
Figure 4:
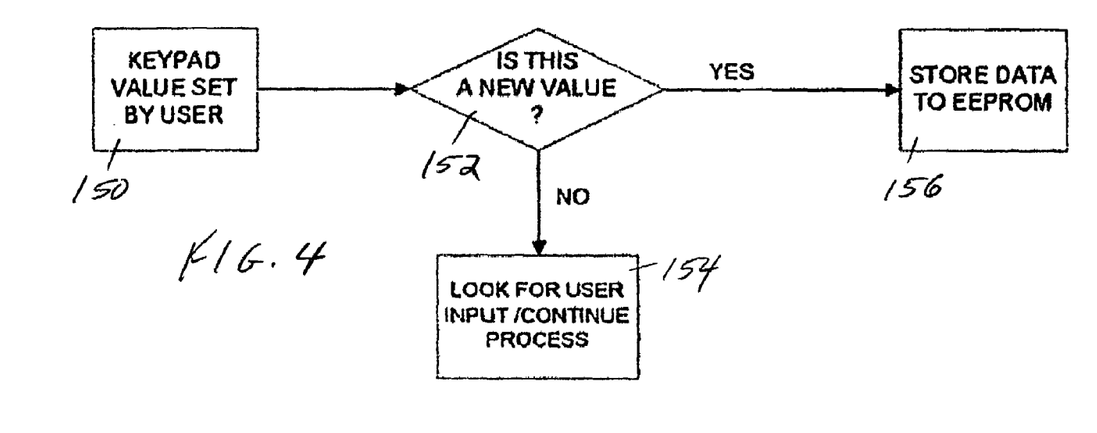

FIGS. 3 and 4 are flow charts illustrating how a procedure condition can be preselected by the surgeon, assuming that the EEPROM has already been programmed to output to the system unit condition-controlling electrical signals when accessed by the μ-controller as taught and shown in FIGS. 9-11 of the '514 patent. The process starts with an initialization software module illustrated at the top of FIG. 3. When the power switch 32 is switched ON 132, the μ-controller represented by block 134 is waked from a sleep or standby state. Under program control, it then seeks the status of the cut mode and cut/coag mode switch 11 (see FIG. 1) represented by test block 140. If that switch was pressed (it is understood that the same routine is executed when the first or second fingerswitch on the fingerswitch handpiece is pressed), then control passes to block 142, which signals the μ-controller 178 (FIG. 10) to clear all power level settings to await a new input from one of the keys of the keypad on the system unit (the keypad refers to the front panel button switches 14). Otherwise, the μ-controller reads 141 any active stored previously-selected power levels, one of the operating conditions for the desired procedure. Now the stored program in the EEPROM when read instructs in a conventional manner the microprocessor to run a sub-routine that outputs to the power level activator (the bias for the output amplifies—see FIG. 6) the appropriate signals to set the power level of the system unit to the value desired for the procedure to be carried out. When the surgeon then applies the active electrode to the surgical site, which can occur as soon as the switch is operated, as the actions by the microprocessor are almost instantaneous compared with the movements of the surgeon, the chosen electrosurgical currents at the desired power are applied to the patient.

Should the surgeon desire to change electrodes or any operating conditions, s/he can then key into the keypad 150 and then control passes to a test block 152 which compares the new value represented by the new input to the stored power level in the EEPROM. If they are the same, control passes to block 154 which awaits any new instructions from the user. If the value inputted is new, then the new values are stored 156 in the EEPROM in same or fresh memory locations for present or future use.

FIG. 6 schematically illustrates the operation where the output mode controller 60, represented in the flow chart of FIG. 2, cooperates with the μ-controller 178 to activate the waveform generators which then send its modulation waveform to the unipolar or bipolar output enabled by the μ-controller as above described.

Summarizing, in the instrument of the invention, normally, the three-button-fingerswitch handpiece controls the three monopolar modes; CUT, CUT/COAG, HEMO; and the triple footswitch controls the two bipolar modes; BIPOLAR HEMO and BIPOLAR TURBO, as well as the monopolar modes. Therefore, these two accessories can control and activate any desired selected operating modes with their preset output power.

Since some surgeons are accustomed to using the footswitch exclusively, if no fingerswitch buttons on the handpiece are pressed, the footswitch can be used to control the CUT and COAG and HEMO modes of both the monopolar and bipolar applications. In a preferred example, color-coding of the triple footswitch, especially when used alone in this mode of operation, will assist the surgeon in choosing the desired operation.

The specific selection of each function (CUT, CUT/COAG, HEMO, BIPOLAR HEMO, and BIPOLAR TURBO) can be manually selected by pressing the switches on the front panel 14 of the unit. In the case of the BIPOLAR TURBO mode, however, the center button 42 of the footswitch is designed to control that function. The center button 42 overrides any manual setting, and always activates the BIPOLAR TURBO mode.

The manual settings of the unit, visible on the display, is the operating mode and power condition activated when the footswitch is activated. All output parameters can be adjusted prior to the surgical operation, obviating the need to go back to the electrosurgical generator making any adjustment during the operation. With the center button 42, which is dedicated to the BIPOLAR TURBO mode, the output can also be controlled to a higher level. This means that the bipolar forceps would normally be the handpiece used. This has the very important advantage that bleeders can be immediately controlled. Bleeders that can unexpectedly arise during a surgical operation require quick attention. With the instrument of the invention, and with the bipolar forceps already plugged into the unit as illustrated in FIG. 1, the surgeon can with confidence simply pick up the bipolar forceps, place the forceps tips on either side of the bleeder, and then simply depress the center button 42, knowing that a level of electrosurgical currents appropriate for shutting off bleeders will immediately be applied to the bleeder for coagulation.

With the 3-button-fingerswitch handpiece, the operating conditions are always determined by the built-in impedances in the handpiece, and always using monopolar electrosurgical currents. Each of the three buttons implements, respectively, CUT, CUT/COAG, and HEMO, three modes for delicate procedures. No activation is required. The depressed button function will be the actual output function; it disregards the front displayed unit pre-setting but activates the appropriate indicator. Preferably, the reaction from the finger-switch handpiece is as follows:

a) Depress first fingerswitch button, it will activate CUT mode;

b) Depress second fingerswitch button, it will activate CUT/COAG mode;

c) Depress third fingerswitch button, it will activate HEMO mode.

Figure 7:
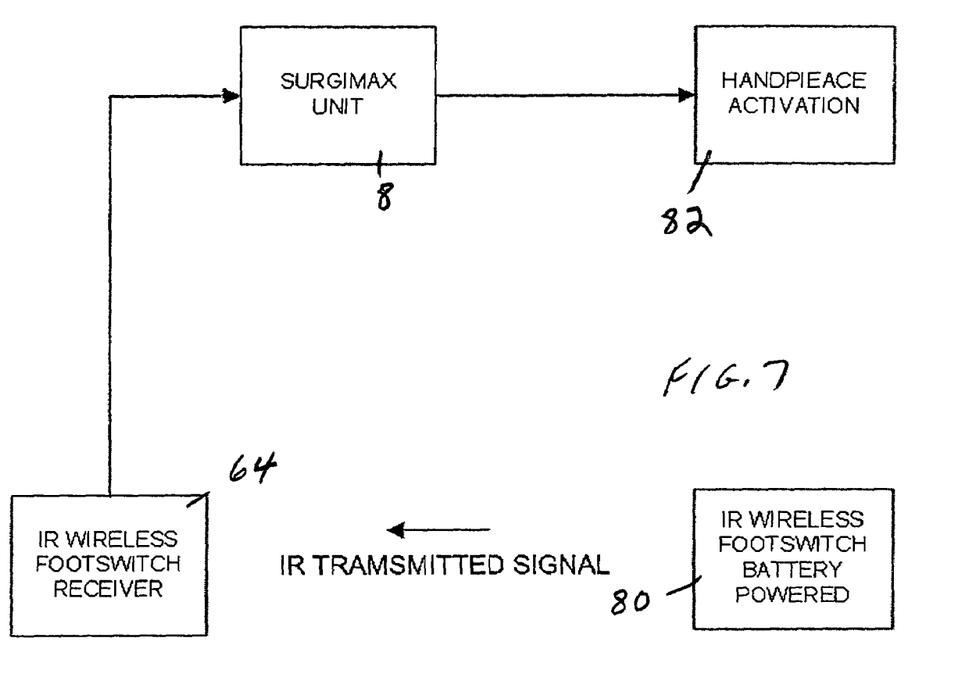
FIG. 7 is a block diagram of showing optional operation of a wireless footswitch for the electrosurgical instrument of FIG. 1.

The instrument will normally be used with cables connecting each of the controllers (handpiece/footswitch) directly to the unit as shown in FIG. 1. However, it will be understood that the use of wireless remote controllers is easily obtained following well-known wireless remote technology widely used in entertainment equipments such as TVs and VCRs. In this case, each of the controllers would be equipped with an infra-red (IR) generator and appropriate circuitry such that a uniquely-encoded IR signal is emitted when a fingerswitch or footswitch is depressed, identical to or decodable into by the unit after detection by a suitable IR sensor to the signal generated and transmitted to the unit when the controller is connected by a cable as described in the '514 patent. A block diagram indicating this operation with the footswitch 80 is depicted in FIG. 7 with the sensor represented by block 64 in FIG. 6. Either handpiece is represented by block 87 in FIG. 7. The operation is straightforward and all the intra- and interconnecting circuitry is well-known in the art. Briefly:

1. Both footswitch and finger-switch controllers 82 may have standard built-in electronic components, cable or wireless remote, corresponding to each particular switch;

2. The electronic sensor 64 picks up the IR signal from these control switches in a first come first served manner;

3. The sensor 64 sends the IR-decoded electrical signal to the microprocessor 178 to request the appropriate action;

4. The microprocessor 178 determines the operational mode from the receiving electrical signal;

5. The determined operational mode is inputted to and causes the waveform generator 62 to trigger the appropriate waveform for the selected mode;

6. The desired waveform is sent to the output mode controller 60 where it is mixed with the appropriate 4.0 or 1.7 MHz carrier and forwarded to the corresponding output terminal 16 or 18 to fulfill the selection from the control switch.

It will be understood that the above example is only a preferred example and other ways of storing and accessing information representing operating conditions of the system unit can be employed. In addition to power levels, a similar approach can be used to automatically set a protective time limit for the desired procedure to ensure that no over cutting or heating inadvertently occurs.

Figure 5:
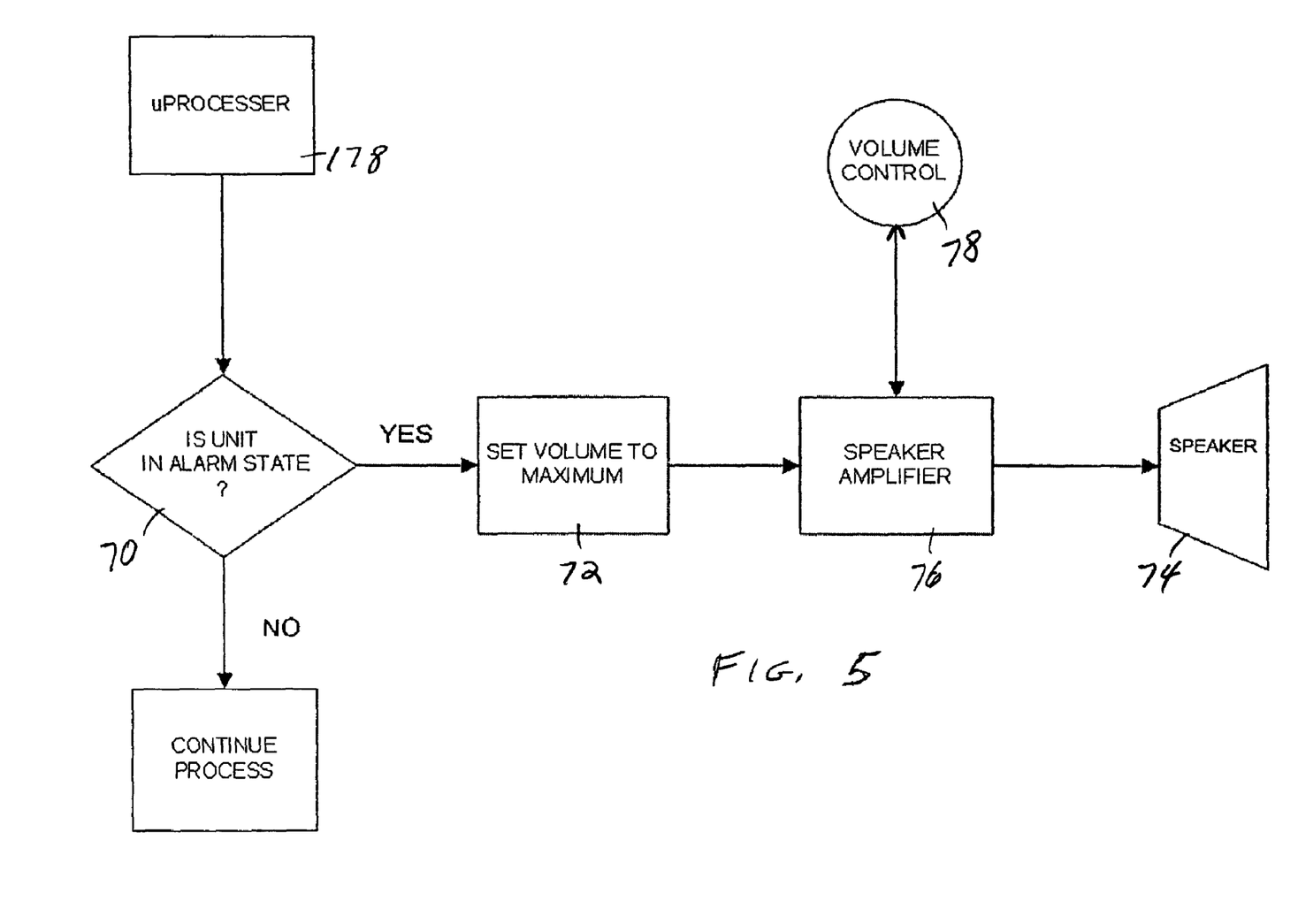
FIG. 5 is a flow chart illustrating software controlled operation of the alarm volume override system.

Other safety provisions can be incorporated into the system of the invention. One such subroutine is illustrated in FIG. 5. A problem can arise that may result in patient harm, if the neutral connection 30 fails, for example, the plug is not seated in its socket 24 or the contact with the patient fails. The instrument of the invention provides a safety system to warn against such a malfunction. A sensor, such as an impedance monitor, is connected to the neutral circuit. Should the impedance measured exceed a safe value, then a signal indicating an alarm state is sent to the μ-controller 178 which calls a routine that first tests 70 whether the alarm state has arisen. If no, the routine ends and the procedure can be resumed. If yes, the routine branches to block 72 to set a speaker 74 in the console 8 to a higher level via a speaker amplifier 78 and a volume control 78. The increase in sound alerts the surgeon that something is amiss and the unit can then be examined for improper connections before proceeding with the surgical procedure.

Figure 8:
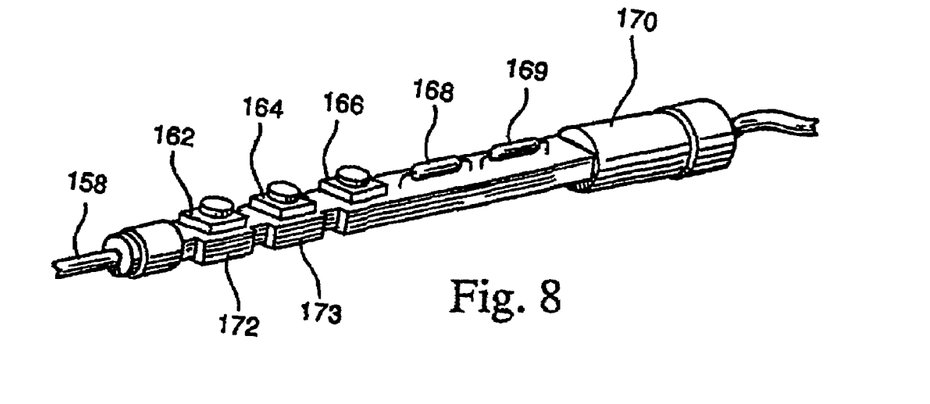
FIG. 8 is a perspective view of one form of three-button-fingerswitch handpiece usable in the invention.
Figure 9:
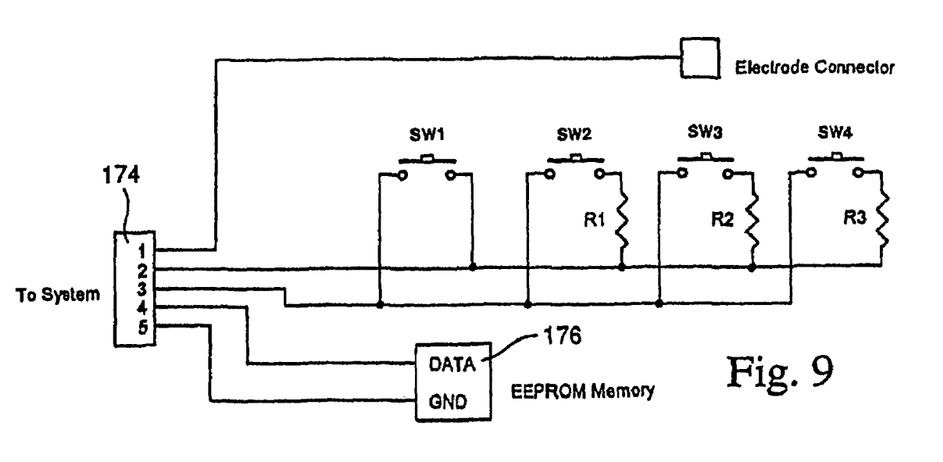
FIG. 9 illustrates the internal circuitry of one form of handpiece for generating control signals for the μ-controller.

FIG. 8 illustrates as an example the internal construction of a handpiece from the '514 patent provided with 3 buttons and 2 internal impedances in the preferred form of resistors and a standard 3-terminal output, and FIG. 9 is the schematic of a 4-button handpiece with 3 internal impedances, an internal non-volatile memory, eg., an EEPROM which may be in the console 8, and a 5-terminal output. The FIG. 9 drawing can also illustrate a 3-button handpiece by simply ignoring or removing the fourth button and the third resistor. The FIG. 8 view is with the housing omitted to show one possible internal construction which comprises in front the electrode holder 158, three finger switches 162, 164, 166, two resistors 168, 169, and a cable holder 170 at the rear which terminates in a 3-terminal connector (not shown). PC boards 172, 173 can also be mounted below as shown if needed.

FIG. 9 illustrates one possible schematic for a 4-button handpiece SW1-SW4 with 3 impedances R1-R3 in the form of resistors. In this embodiment, a 5-terminal connector 174 is provided to increase the number of control signals that can be accommodated, as well as provide connections to an internal or external EEPROM 176 as explained. It is understood that the invention is not limited to separate connections for the finger switches and the EEPROM. As is well known in the microprocessor used in watches, the same button or key can be used for different functions by having the microprocessor sense multiple button presses, and associate for example function A with one key press and function B with two quick presses of the same key, and the same approach can be used in the invention but the illustrated arrangement is preferred.

The preferred embodiment uses 100/150 ohm resistances for the mode selection resistors 168, 169, respectively. With an AC current established at the upper two terminals of about 70 mA when for example the fingerswitch 162 is closed, when instead the fingerswitch 164, 166, respectively, is closed, the introduction of the series resistor 168, 169, respectively, reduces the DC current to about 3, 2, respectively, mA. This difference is sufficient to be detected and when amplified or digitized can be used to control the microcontroller. However, it will be apparent to those skilled in the art that the choice of resistance depends upon a number of factors including the type of microcontroller used and the circuit components between the microcontroller and the handpiece, and other resistance values would be appropriate with other circuits and is deemed within the scope of the invention.

A block diagram illustrating the interfacing arrangement of a microcontroller to the handpiece was shown in FIG. 10. With the microcontroller 178 connected via conventional optical isolation 179 to the handpiece 180. The microcontroller 178 can communicate through a serial protocol to the EEPROM 182 incorporated inside the handpiece 180 or instrument. Optical isolation is desirable to protect the processor 178 from RF noise generated while the instrument's output is active. The memory 182 in the handpiece can be read from and written to by the processor 178 to allow the handpiece to store a variety of configuration and operational information.

It will be understood that the invention is not limited to resistors as other small size impedances could be substituted capable of sufficently changing the DC or AC current level upon activation of one or the other fingerswitch.

While the preferred mode of operation includes RF power in a frequency range exceeding 1 MHz, 1.7-4 MHz being preferred, the invention is not so limited and other frequency ranges for electrosurgical procedures are also considered within the scope of the invention.

What has so far been described is how a novel construction of the handpiece can be used to generate a control signal to operate a μC which then controls the electrosurgical instrument to provide the correct mode of RF operating currents to the handpiece. It will be understood that the symbol for a microcomputer μC is also used herein to signify a microcontroller or microprocessor (the terms are used interchangeably), commercial embodiments of which both contain for all practical purposes the same computing elements including a ROM to store a program in the usual way. Three buttons of the handpiece are used to select the different operating modes, but the invention is not limited to three-button handpieces but also includes handpieces with one or more additional buttons.

A further example of how the selected mode, power, and time can be actually implemented in the instrument is illustrated by the flow chart in FIG. 11. Recall that the handpiece need not be limited to remembering or setting modes and power levels but must cooperate with the local electrosurgical instrument to provide the functions as described above. It will work with a standard handpiece having 2 or no buttons. Some of those functions are illustrated in the flow chart of FIG. 11. The starting point is the initialization block 184. If no handpiece, sometimes referred to for brevity herein as "probe", has been connected to the instrument or it is unconfigured 186, the program branches to block 187 to check whether a probe has been connected. If the answer is no, the program loops back to block 187. If the answer is yes, the program falls through to block 188 to check whether the system is configured. If the answer is no, then, under control of the program, the system controller 178 accesses the EEPROM 182, reads 189 the EEPROM settings, and at block 190 then configures the instrument (system) to the correct mode and condition settings. The program then returns to block 187, proceeds then to block 188 and branches to the right to the block 192 which allows operation including display of the operating parameters to the user based on the EEPROM settings.

In the read probe block 189, the μC receives an unambiguous indication of what buttons are physically on the probe and what modes they initiate. A probe could be configured to allow a unit to work only in one or certain modes, and could also be configured to allow the electrosurgical unit to put out only certain ranges of power in each allowed mode. In addition, the probe memory 182 could be used to implement the number of uses or elapsed time of use functions. A new probe might be set to 50 uses or 100 minutes of use to retain its reliability. When a probe has run out of time/uses it could be recharged (reprogrammed) or thrown away. The probe is typically factory-configured to define the above information. The instrument reads the probe data and configures itself. The hardware used to interface the handpiece to the instrument can be the same as that described in connection with FIGS. 1-10 above.

The mode and condition-setting functions can be incorporated in the probe or handpiece as just described or in the electrosurgical instrument or in both. In the case of the electrosurgical instrument, there are a number of different ways in which a handpiece key press or 2 key presses can select the mode and conditions of a particular procedure. One way is to incorporate in the instrument a conventional look-up table that contains the mode and operating conditions for a number of different procedures, with the look-up table responding to a particular control signal (key) from the handpiece to vector to a subroutine which, equivalent to the surgeon's activation of the front panel switches, automatically switches the electrosurgical instrument to the correct mode and sub-mode and automatically sets the power to a specific value or optionally to allow a specific range of values that will not harm the patient. A timer can also be included in the electrosurgical instrument so that the ON time of the instrument does not exceed a maximum time for the application of electrosurgical currents to the patient undergoing that procedure. As one example, a handpiece can be provided that is tailored for surgical procedures carried out with the instrument set at the cutting mode and the Cut or Cut/Coag sub-mode. The handpiece has incorporated in it a known blade electrode. For many cutting procedures, a typical power setting for tissue incisions is, say, 10 Watt, and a typical cutting duration rarely exceeds 10 sec. The handpiece tailored for cutting has a resistor of say 40 ohms connected to finger switch-2, and a resistor of say 30 ohms connected to finger switch-3. So, when finger switch-2 is pressed, a control signal of, say, 20 mA is sent to the instrument housing the μC and when finger switch-3 is pressed, a control signal of 30 mA is sent to the instrument housing the μC.

The mode selection and power settings is a straight forward implementation using the principles and circuitry described in connection with FIGS. 1-11. The look-up table is an example of a database as a set of records each including an identifying key to uniquely identify the record. In the relatively small database involved here, it can be implemented as an unordered list in which any record is easily accessed by inputting an identifying key which then outputs the record. The key here is the control signal generated by a particular key press, converted to a digital number, and the record outputted could be, for example, a digital word the individual bits of which or combinations of bits represent a mode, sub-mode or mode condition (explained below). Alternatively, the database can be implemented as a table of records indexed by identifying keys, either as a 1-dimensional table or as a list of records. In either case, the inputted key produces a unique output record. The specific way of accomplishing outputting of records upon inputting of keys is not part of the present invention and is well known in the art.

It is preferred that the selected function be confirmed to the physician after the selection has been made by the instrument displaying the pre-set function on the display panel to inform the user of its current mode and output setting.

To summarize the manner of using the instrument of the invention:

1. Note that five modes of electrosurgical currents are displayed on the face of the panel, each of which can be selected by a user depressing one of the mode selecting switches 11, 12.

2. When the unit is turned on, the routine represented by FIG. 3 is executed. If neither mode selection switch is pressed, the current stored EEPROM power level is read. When the unit is used, with the same handpiece or footswitch last used, the same preset-current power level is delivered.

3. If one of the switches is pressed, then the stored power level is cleared and the unit awaits another action by the user. When a keypad value is entered, meaning that one of the up/down switches 14 are pressed, the routine represented by FIG. 4 is executed. Any new data is stored for that particular mode.

4. The user can repeat the sequence of steps for each of the five operating modes, and thus the different operating power levels for each of the modes is stored in the EEPROM and thus preset in the instrument before the procedure is commenced.

5. Now, the user can pickup and apply the 3-button fingerswitch handpiece 22. The three buttons each are connected via hard wiring to input a signal to the μ-controller that it can interpret to mean generate and deliver a particular waveform to the electrode at the preset power level. Thus, the first button can be used for the unipolar CUT mode, the second button can be used for the unipolar CUT/COAG mode, and the third button can be used for the unipolar HEMO mode. When the mode is selected in this way, a corresponding light is lit on the front panel display 34. A similar result will apply when the user instead depresses the left footswitch 38 and then the CUT mode or the CUT/COAG mode is selected at their own respective preset power level depending upon which of the corresponding lights are lit on the front panel displays 34 at the time that the footswitch is pressed. Note that the fingerswitches on the unipolar handpiece 22 determine the mode, whereas with the footswitch, the user selects from the front panel the operating mode.

6. If the user picks up and applies the bipolar handpiece 24 after the user has chosen the bipolar HEMO mode from the front panel, then only the bipolar HEMO mode is selected and the μ-controller will generate and deliver the HEMO waveform-modulated carrier to the electrode at the preset power level. The identical result follows when the user instead depresses the right footswitch 40.

7. Finally, if the user instead depresses the center footswitch 42 then the bipolar TURBO mode is selected at its own preset power level and the corresponding light is lit on the front panel displays 34.

The instrument described and claimed in this application uniquely differs from the instrument described in the two referenced patents in at least the following ways:

1. Any electrode connected to the monopolar output connector always receives only high frequency monopolar electrosurgical currents, 2. Any electrode connected to the bipolar output connector can receive only low frequency bipolar electrosurgical currents.

3. The fingerswitches on the fingerswitch handpiece can activate cut, cut/coag and hemo monopolar electrosurgical currents, 4. A footswitch on the triple footswitch can control cut, cut/coag and hemo monopolar, electrosurgical currents, 5. A footswitch on the triple footswitch can control low frequency low power bipolar electrosurgical currents for coagulation directed to the bipolar output connector.

6. A footswitch on the triple footswitch can control low frequency high power bipolar TURBO mode electrosurgical currents directed to the bipolar output connector.

7. Operating power levels can be preset into the instrument for each of the operating modes, and the instrument will remember the last-used power level for each mode.

8. A new electrosurgical current called bipolar TURBO is introduced, which has a higher power output than bipolar HEMO, but a smaller duty cycle, using a gradually-increasing then decreasing burst of amplitude-modulated 1.7 MHz carrier. This is important in those surgical interventions where larger bleeders are present such as abdominoplasty where immediate hemostasis is required. In contrast, bipolar HEMO is useful for many procedures where bleeding control is necessary and critical anatomy is close by. An example would be a face lifting dissection and bleeding within the face anatomy where transection of the facial ligament without damage to the facial nerve is important.

9. Increased RF output power enables the instrument to address larger bleeders and highly fibrous tissue in both monopolar and bipolar modes. In addressing larger skin, muscle, and fibrous fat tissue, immediate and positive stopping of bleeders and the smooth efficient ability to incise, dissect, and section, layer by layer, is critically important. Additional power wattage is important and necessary to avoid necrosis of tissue and retraction of flaps.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical instrument having a plurality of operating modes and at least one operating condition including power output associated with each of the operating modes comprising:
    (a) a console unit (8) having a monopolar output connector (16) and a bipolar output connector (18),
    (b) instrument controllers comprising
        i) a monopolar fingerswitch handpiece (22) connected to the monopolar output connector,
        ii) a footswitch (28) connected to the instrument,
    (c) a bipolar handpiece (24) connected to the bipolar output connector,
    (d) circuitry in the console unit for generating first (108) and second (102) different RF electrosurgical currents each selectively modulated by different selected waveforms, the monopolar output connector being connected (84) to receive the first RF electrosurgical currents, the bipolar output connector (86) being connected to receive the second RF electrosurgical currents, the selected waveforms comprising:
        (i) three waveforms configured when applied to tissue by the monopolar fingerswitch handpiece (22) connected to the monopolar output connector to perform, respectively, CUT, CUT/COAG, and HEMO procedures, and
        (ii) two different waveforms configured when applied to tissue by the bipolar handpiece (24) connected to the bipolar output connector to perform, respectively, two different HEMO procedures,
    (e) a nonvolatile memory (182) for storing information representative of the operating condition,
    (f) the monopolar fingerswitch handpiece and footswitch are connected when operated (92) to activate the circuitry for generating the first and second RF electrosurgical currents,
    (g) switch means connected to the console for presetting (156) into the memory information representative of the operating condition for all of the operating modes,
    (h) electronic means in response to operation of one of the instrument controllers for retrieving (141) the stored information representative of the operating condition associated with and setting the operating condition for the operated controller,
    (i) the selected waveforms being combined with the first and second RF electrosurgical currents to provide operating modes including three monopolar modes (110, 112, 114) for performing, respectively, CUT, CUT/COAG, and HEMO procedures available at the monopolar output connector and two different bipolar modes (104) for performing, respectively, two different HEMO procedures available at the bipolar output connector.

2. An electrosurgical instrument as claimed in claim 1, wherein the monopolar fingerswitch handpiece has three operating buttons (162, 164, 166) each connected to the console unit to select and activate one of the monopolar modes with the first electrosurgical currents.

3. An electrosurgical instrument as claimed in claim 1, wherein:
    the first RF electrosurgical currents has a higher frequency than the second RF electrosurgical currents.

4. The instrument according to claim 3, wherein the RF electrosurgical currents are in the 1-4 MHz range.

5. The instrument according to claim 4, wherein the first RF electrosurgical currents is about 4 MHz, and the second RF electrosurgical currents is about 1.7 MHz.

6. An electrosurgical instrument as claimed in claim 1, wherein one of the bipolar modes comprises second electrosurgical currents at a relatively low power that are half-wave rectified and unfiltered, and the other of the bipolar modes comprises second electrosurgical currents as short bursts at a relatively high power.

7. An electrosurgical instrument having a plurality of operating modes and at least one operating condition including power output associated with each of the operating modes comprising:
    (a) a console unit (8) having a monopolar output connector (16) and a bipolar output connector(18),
    (b) instrument controllers comprising
        i) a monopolar fingerswitch handpiece (22) connected to the monopolar output connector,
        ii) a footswitch (28) connected to the instrument,
    (c) a bipolar handpiece (24) connected to the bipolar output connector,
    (d) circuitry in the console unit for generating first (108) and second (102) different RF electrosurgical currents each selectively modulated by different selected waveforms, the monopolar output connector being connected (84) to receive the first RF electrosurgical currents, the bipolar output connector (86) being connected to receive the second RF electrosurgical currents, the selected waveforms comprising:
        (i) three waveforms configured when applied to tissue by the monopolar fingerswitch handpiece (22) connected to the monopolar output connector to perform, respectively, CUT, COT/COAG, and HEMO procedures, and
        (ii) two waveforms configured when applied to tissue by the bipolar handpiece (24) connected to the bipolar output connector to perform two different HEMO procedures,
    (e) a non-volatile memory (182) for storing information representative of the operating condition,
    (f) the monopolar fingerswitch handpiece and footswitch are connected when operated (92) to activate the circuitry for generating the first and second RF electrosurgical currents,
    (g) switch means connected to the console for presetting (156) into the memory information representative of the operating condition for all of the operating modes,
    (h) electronic means in response to operation of one of the instrument controllers for retrieving (141) the stored information representative of the operating condition associated with and setting the operating condition for the operated controller,
    (i) the selected waveforms being combined with the first and second RF electrosurgical currents to provide operating modes including three monopolar modes (110, 112, 114) for performing, respectively, CUT, CUT/COAG, and HEMO procedures available at the monopolar output connector and two bipolar modes (104) for performing, respectively, two different HEMO procedures available at the bipolar output connector, (j) the monopolar fingerswitch handpiece having three operating buttons (162, 164, 166) each connected to the console unit to select and activate one of the monopolar modes with the first electrosurgical currents, (k) the footswitch having three operating positions (38, 40, 42) each connected to the console unit to select and activate monopolar and bipolar modes.

8. An electrosurgical instrument having a plurality of operating modes and at least one operating condition including power output associated with each of the operating modes comprising:

(a) a console unit (8) having a monopolar output connector (16) and a bipolar output connector (18), (b) instrument controllers comprising
 i) a monopolar fingerswitch handpiece (22) connected to the monopolar output connector,
 ii) a footswitch (28) connected to the instrument, (c) a bipolar handpiece (24) connected to the bipolar output connector, (d) circuitry in the console unit for generating first (108) and second (102) different RF electrosurgical currents each selectively modulated by different selected waveforms, the monopolar output connector being connected (84) to receive the first RF electrosurgical currents, the bipolar output connector (86) being connected to receive the second RF electrosurgical currents, the selected waveforms comprising:
 (i) three waveforms configured when applied to tissue by the monopolar fingerswitch handpiece (22) connected to the monopolar output connector to perform, respectively, CUT, CUT/COAG, and HEMO procedures, and
 (ii) two waveforms configured when applied to tissue by the bipolar handpiece (24) connected to the bipolar output connector to perform two different HEMO procedures, (e) a non-volatile memory (182) for storing information representative of the operating condition, (f) the monopolar fingerswitch handpiece and footswitch are connected when operated (92) to activate the circuitry for generating the first and second RF electrosurgical currents, (g) switch means connected to the console for presetting (156) into the memory information representative of the operating condition for all of the operating modes, (h) electronic means in response to operation of one of the instrument controllers for retrieving (141) the stored information representative of the operating condition associated with and setting the operating condition for the operated controller, (i) the selected waveforms being combined with the first and second RF electrosurgical currents to provide operating modes including three monopolar modes (110, 112, 114) available at the monopolar output connector and two bipolar modes (104) available at the bipolar output connector, (j) the monopolar fingerswitch handpiece comprising first, second, and third operating buttons (162, 164, 166) each connected to the console unit to select and activate one of the monopolar modes with the first electrosurgical currents, (k) the footswitch comprising first, second, and third switches (38, 40, 42) each connected to the console unit to select and activate monopolar and bipolar modes, (l) the electronic means including software in the instrument:
 i) in response to activation of the first fingerswitch button for directing the first RF electrosurgical currents in the CUT mode (110) to the monopolar output connector,
 ii) in response to activation of the second fingerswitch button for directing the first RF electrosurgical currents in the CUT/COAG mode (112) to the monopolar output connector,
 iii) in response to activation of the third fingerswitch button for directing the first RF electrosurgical currents in the HEMO mode (114) to the monopolar output connector,
 iv) in response to activation of the first footswitch switch (38) for directing the first RF electrosurgical currents to the monopolar output connector,
 vi) in response to activation of the second footswitch switch (40) for directing the second RF electrosurgical currents to the bipolar output connector,
 vii) in response to activation of the third footswitch switch (42) for directing the second RF electrosurgical currents to the bipolar output connector, whereby the first RF electrosurgical currents (108) are always directed to the monopolar output connector and the second RF electrosurgical currents (102) are always directed to the bipolar output connector however selectively modulated.

9. An electrosurgical instrument as claimed in claim 8, wherein one of the bipolar modes generated in response to activation of the second footswitch switch comprises second electrosurgical currents at a relatively low power that are half-wave rectified and unfiltered, and the other of the bipolar modes generated in response to activation of the third footswitch switch comprises second electrosurgical currents as short bursts of changing amplitude at a relatively high power.

* * * * *